United States Patent
Lee

(10) Patent No.: US 6,524,537 B1
(45) Date of Patent: Feb. 25, 2003

(54) FRAGRANCE EMITTER FOR USE WITH INTERNET

(76) Inventor: Chum Lee, No. 39-5, Gau Gaung Road, Yung-He, Taipei (TW)

( * ) Notice: Subject to any disclaimer, the term of this patent is extended or adjusted under 35 U.S.C. 154(b) by 0 days.

(21) Appl. No.: 09/519,685

(22) Filed: Mar. 7, 2000

(30) Foreign Application Priority Data

Aug. 4, 1999 (TW) ..................................... 088213100 U

(51) Int. Cl.[7] ................................................. A62B 7/08
(52) U.S. Cl. ....................... 422/124; 364/502; 364/509; 364/514 A; 422/108; 422/116; 422/119; 422/120; 422/123
(58) Field of Search ........................... 422/1, 4, 5, 108, 422/116, 119, 120, 123, 124; 364/502, 509, 514 A

(56) References Cited

U.S. PATENT DOCUMENTS

| | | | | |
|---|---|---|---|---|
| 5,114,625 A | * | 5/1992 | Gibson | 261/102 |
| 5,174,967 A | * | 12/1992 | Fukuhara | 261/65 |
| 5,565,148 A | * | 10/1996 | Pendergrass, Jr. | 261/30 |
| 5,591,409 A | * | 1/1997 | Watkins | 422/1 |
| 5,724,256 A | * | 3/1998 | Lee et al. | 422/105 |
| 5,734,590 A | * | 3/1998 | Tebbe | 700/94 |
| 5,924,597 A | * | 7/1999 | Lynn | 222/1 |
| 5,972,290 A | * | 10/1999 | De Sousa | 422/123 |
| 6,053,738 A | * | 4/2000 | Ivey, Jr. | 273/460 |

* cited by examiner

*Primary Examiner*—Krisanne Thornton
(74) *Attorney, Agent, or Firm*—Ostrolenk, Faber, Gerb & Soffen, LLP

(57) ABSTRACT

A fragrance emitter used with internet is disclosed. The fragrance emitter is able to emit various kinds of fragrance stored in vessels according to the command sent by a frequency detector which is used to search for the existence of a specific frequency specially used by a specific web site. Therefore, when the existence of a specific frequency matches with a predetermined frequency, the electromagnetic valve is able to activate the movement of a valve mounted on a fragrance vessel in an air tight manner, such that the fragrance is ventilated and mix with the air by a fan.

4 Claims, 5 Drawing Sheets

FRAGRANCE EMITTER FOR USE WITH INTERNET

BACKGROUND OF THE INVENTION

1. Field of the Invention

The present invention relates to a fragrance emitter, and more particularly to a fragrance emitter for use with internet or television programs. The fragrance emitter is able to emit various kinds of fragrance stored in vessels according to the command sent by a frequency detector which is used to search for the existence of a specific frequency specially used by a specific web site.

2. Description of Related Art

Because the continuous pursuit of speed in data processing, the generation of computers open a new era for mankind. Users use computer to search for data, communicating with others, placing orders, paying tax . . . etc. However, all these interactions between the user and the computer are limited only to pictures and sound, which is quite boring to a user after quite a long period of time sitting behind or in front of the monitor. To solve the problem, increasing the interactive action between the user and the internet seems to be the only answer. Therefore, the present invention tends to provide a fragrance emitter used with internet so as to mitigate and obviate the aforementioned problems.

SUMMARY OF THE INVENTION

The main objective of the invention is to provide a fragrance emitter, which has an audio frequency decoder to detect the variation of the web site, such that when the audio frequency decoder detected the existence of a specific frequency, the fragrance emitter is activated to emit a fragrance corresponding to the specific frequency.

Another objective of the invention is to provide a fragrance emitter which is able to be used with products such as perfume to promote the popularity of this product.

Other objects, advantages and novel features of the invention will become more apparent from the following detailed description when taken in conjunction with the accompanying drawings.

DETAILED DESCRIPTION OF PREFERRED EMBODIMENT

Figure 1:
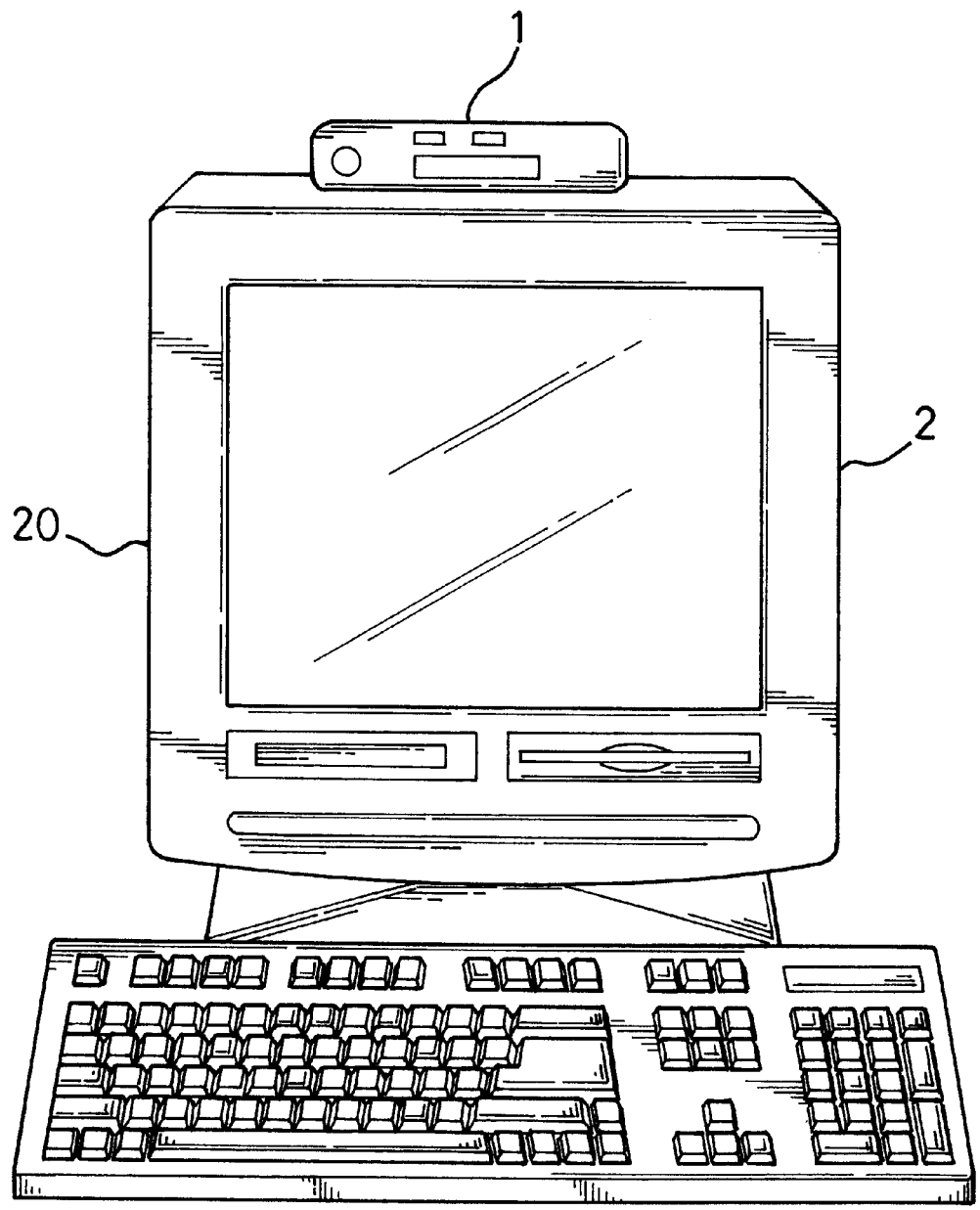
FIG. 1 is a schematic view showing a computer connected with a fragrance emitter in accordance with the present invention.

The invention relates to a fragrance emitter used with internet. The fragrance emitter is able to send out various kinds of fragrance according to the command sent by a frequency detector which is used to search for the existence of a specific frequency specially used by a specific web site. With reference of FIG. 1, the computer connecting with the fragrance emitter 1, a internet user executes the browser software to browse different web sites which can send out a specific frequency through the internet. The specific frequency can be detected by a frequency detector and thus activate the dispensing of a specific fragrance. The principle and theory will be described hereinafter.

Figure 2:
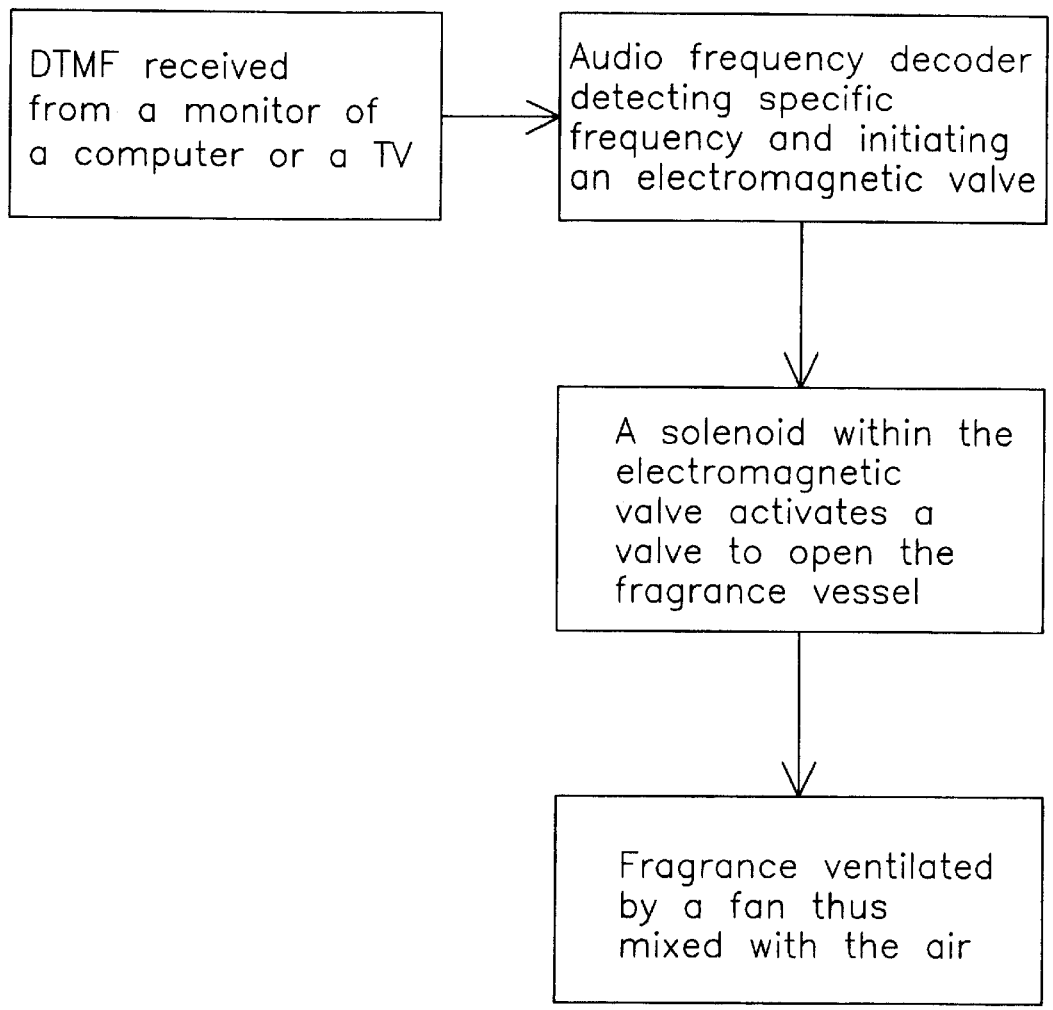
FIG. 2 is a flow chart showing the commanding sequence of the fragrance emitter.

With reference to FIG. 2, it is to be noted that when a dual tone multi-frequency (DTMF) is received by a monitor of a computer or a television, a frequency detector will detect for the existence of a specific frequency. When the specific frequency is detected by the frequency detector, the frequency detector will send out a signal to initiate a corresponding output port. The port will then activate an electromagnetic valve to open a vessel containing fragrance therein. Thereafter, a fan driven also by the signal sent by the frequency detector will ventilate the fragrance through an air duct to the air.

Figure 3:
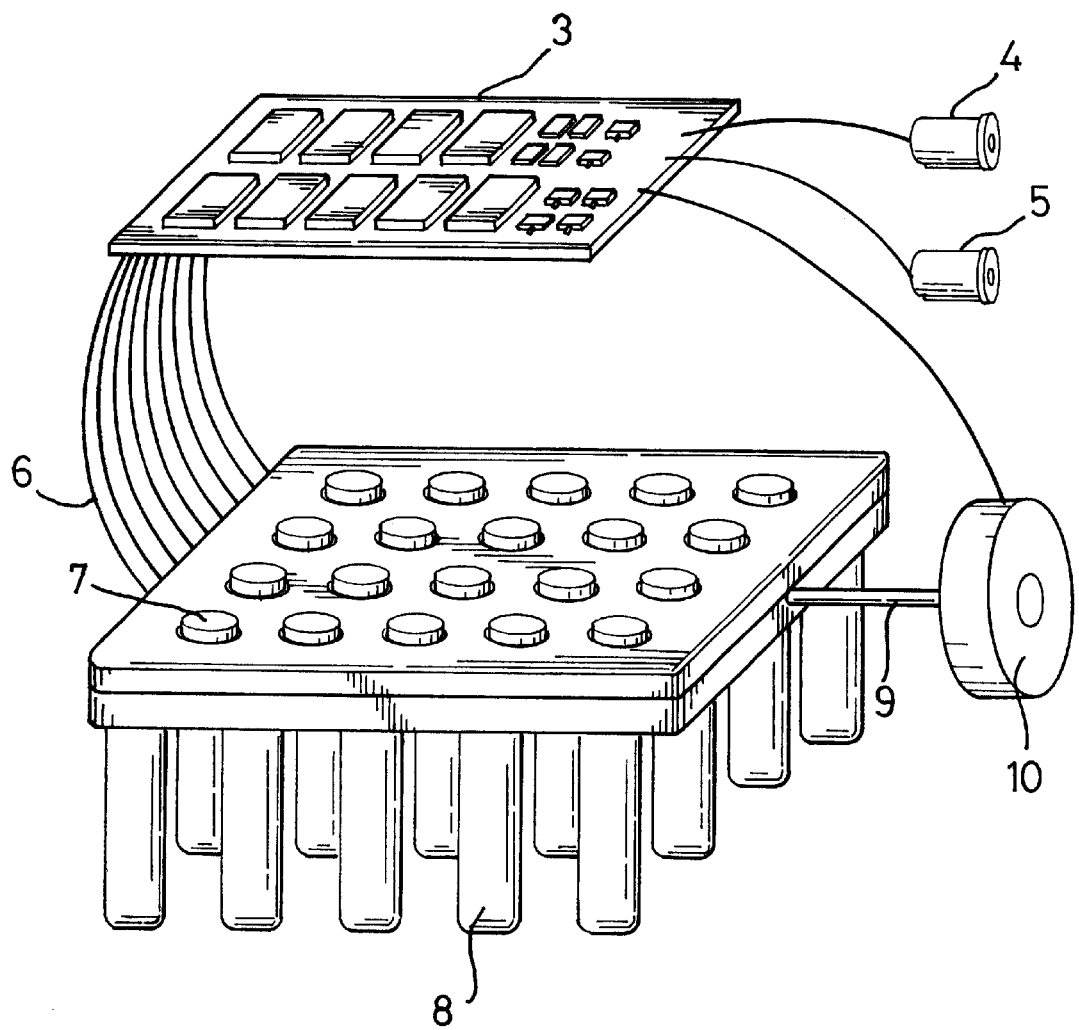
FIG. 3 is a preferred embodiment showing the parts of the fragrance emitter of the invention.
Figure 4:
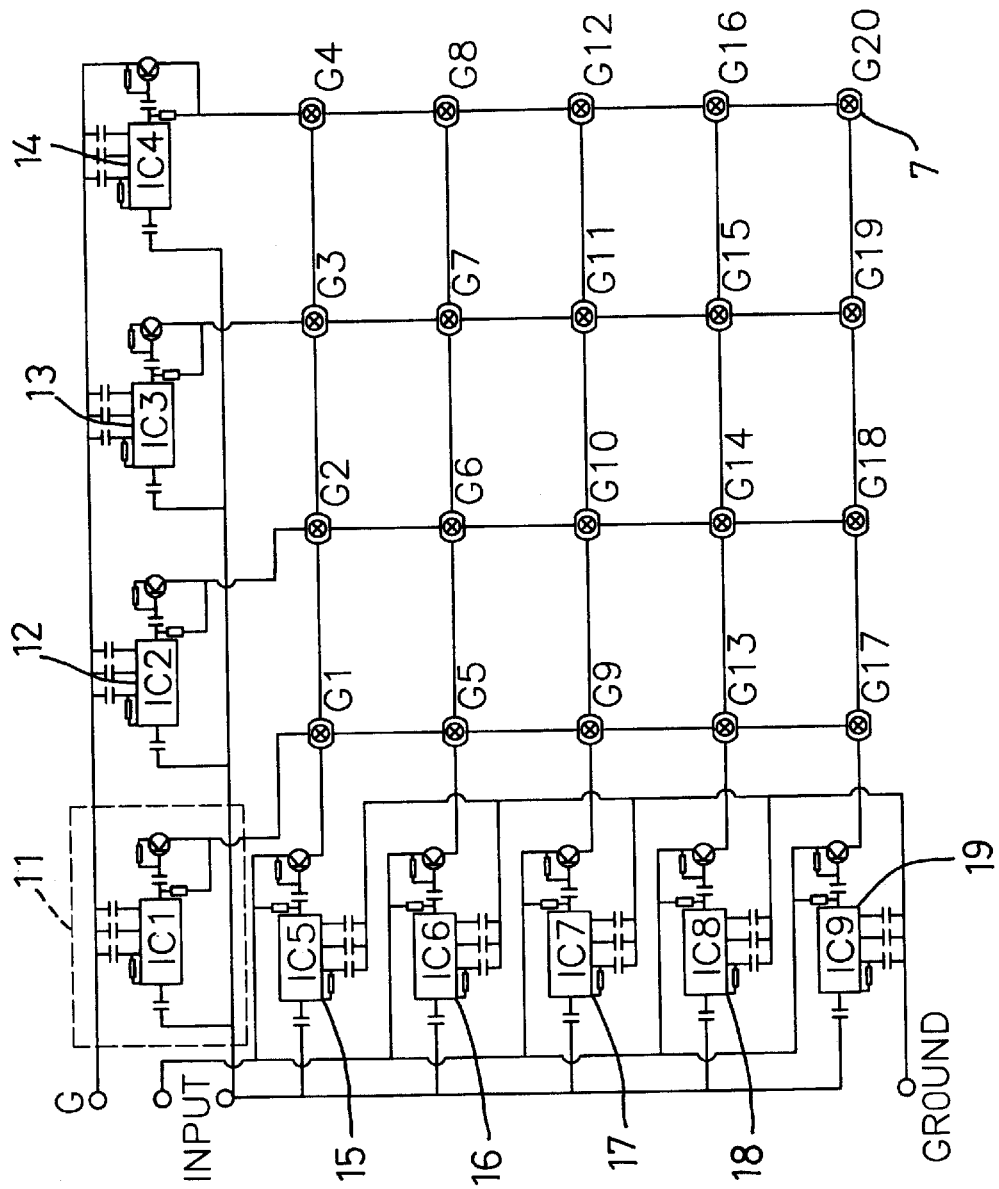
FIG. 4 is a circuit used in the fragrance emitter as shown in FIG. 3.
Figure 5:
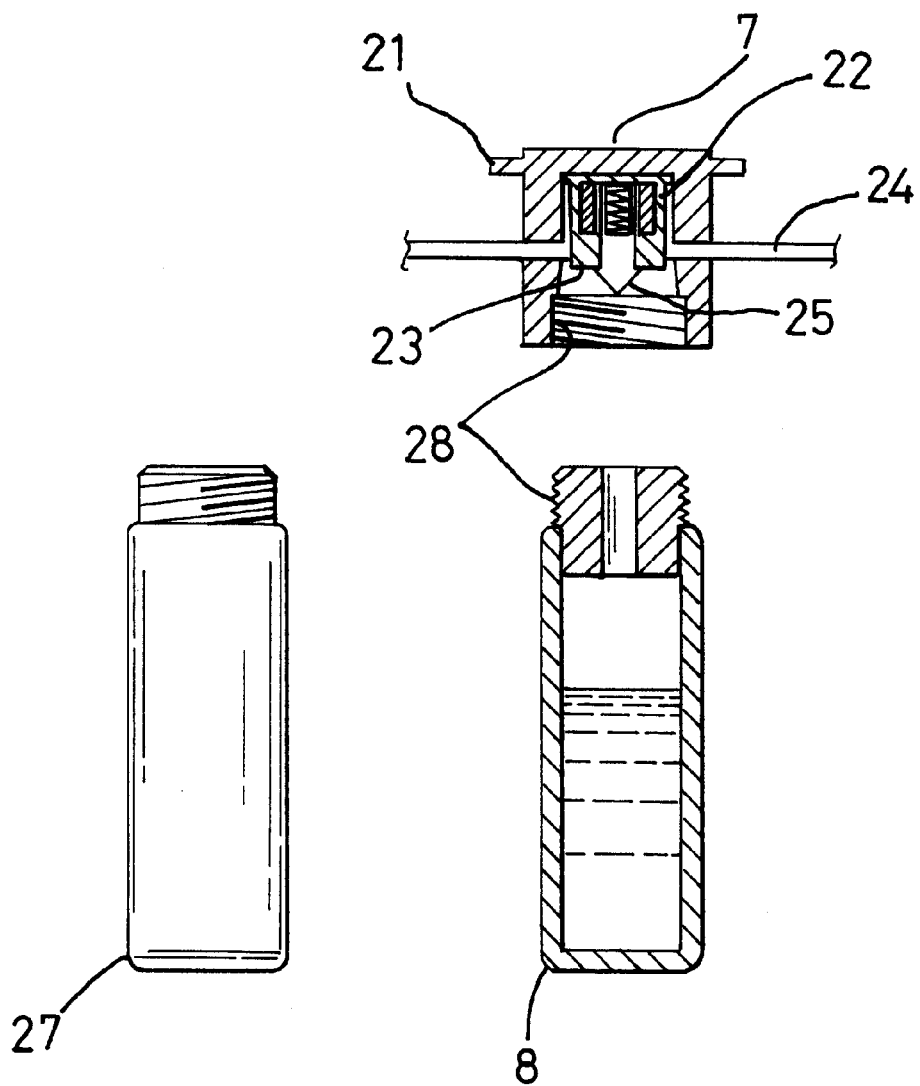
FIG. 5 are cross sectional views of the electromagnetic valve and the fragrance emitter.

With reference to FIGS. 3 to 5, when the fragrance emitter is in use, a connector 4 is connected to a DC power source, and a second connector 5 is used to receive a signal. The audio frequency decoder (11~19) on the circuit board 3 will detect and examine an incoming (input) signal to cycle an electromagnetic valve 7 corresponding to the incoming signal. A cable 6 is connected between the circuit board 3 and the electromagnetic valve 7 such that different signals will have a unique route to be transmitted to the corresponding electromagnetic valves 7. When the audio frequency decoder (11~19) detects the existence of a specific frequency, and simultaneously sends out a signal to the corresponding electromagnetic valve 7, a fan 10 will also be activated to blow the fragrance particles. With reference especially to FIG. 5, when the electromagnetic valve 7 receives a signal from the audio frequency decoder (11~19), a solenoid 22 in the electromagnetic valve 7 will move a valve disk 25 under a cover 21 from an opening (not numbered) in a hollow vessel 8 to enable the particles of fragrance in the vessel 8 to be drawn by the fan 10 to an air duct 24. Eventually, the fragrance particles in the air duct 24 will be blown into the air (e.g. 1~2 meters in front of the monitor or emitter).

Taking one example for instance, the DTMF of the fragrance of a rose is (541Hz, 943Hz). When the DTMF of the rose is picked up from the monitor of a computer or a television, the DTMF will be sent to the fragrance emitter 1. The audio frequency decoder IC 4: LM 567 14 used to detect the existence of the frequency 541 Hz and IC 9: LM567 19 used to detect the existence of the frequency 943 Hz will instantly detect the existence of this particular DTMF. After which, the solenoid 22 will be activated to move the valve disk 25 away from the opening in the vessel 8 to allow the fragrance particles to be blown by the fan 10 to the air duct 24 from an exit 23.

With the arrangement described above, the fragrance emitter 1 in accordance with the present invention is able to be combined with the internet, which enhances the interaction between the internet user and the web site, such that business men are able to use the fragrance emitter of the invention in commercial promotion. Furthermore, the number of the vessels 8 is determined according to the personal preference. Therefore, there is no limit to the number of the vessels 8.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A fragrance emitter for use with the Internet, comprising:
   a circuit board having a first connector for connecting to a DC power source, a second connector for receiving incoming signals from an Internet web site and an audio frequency decoder mounted on said circuit board for detecting a specific frequency of said incoming signals;
   an electromagnetic valve receiving signals from said audio frequency decoder when said audio frequency decoder detects said specific frequency, the valve including a valve disk and the decoder then initiating the movement of the valve disk, wherein said electromagnetic valve has a solenoid mounted in said valve and connected to move said valve disk, and has an air duct with an exit and a fan mounted in said air duct; whereby when said valve disk is moved by the activation of said solenoid, said fan is also activated to start blowing the air in said air duct toward said exit, such that said fragrance is able to be blown by said fan into the air;
   at least one vessel containing at least one fragrance and having said valve disk mounted on said vessel in an air tight manner; whereby when said valve disk is moved by said electromagnetic valve, said fragrance is able to mix with the air.

2. A fragrance emitter for use with the Internet, comprising:
   a circuit board having a first connector for connecting to a DC power source, a second connector for receiving incoming signals and an audio frequency decoder mounted on said circuit board for detecting a specific frequency of said incoming signals;
   at least one vessel containing at least one fragrance, said at least one vessel having an electromagnetic valve, an air duct having an exit, and a valve disk mounted on said at least one vessel in an air tight manner;
   an air tube in communication with a fan and with said air duct of said at least one vessel; and
   a solenoid mounted in said electromagnetic valve, said electromagnetic valve being adapted to receive signals from said audio frequency decoder when said audio frequency decoder detects said specific frequency, said valve disk is movable initiated by the activation of said solenoid and opening said at least one vessel enabling said fragrance to enter said valve air duct, and said fan is also activated to start blowing the air in said air tube such that said fragrance is blown by said fan into the air, to mix with the air.

3. The fragrance emitter as claimed in claim 2, wherein said incoming signals are from an Internet web site.

4. The fragrance emitter as claimed in claim 2, wherein said incoming signals are from a television program.

* * * * *